US00PP07827P

United States Patent [19]

Chamberlin, Sr.

[11] Patent Number: Plant 7,827

[45] Date of Patent: Mar. 17, 1992

[54] 'OCTOBER SUN' PLUM TREE

[75] Inventor: Thomas O. Chamberlin, Sr., Visalia, Calif.

[73] Assignee: Metropolitan Life Insurance Company, Overland Park, Kans.

[21] Appl. No.: 526,113

[22] Filed: May 21, 1990

[51] Int. Cl.[5] ..... A01H 5/00

[52] U.S. Cl. ..... Plt./38

[58] Field of Search ..... Plt./38, 38.1

*Primary Examiner*—Howard J. Locker

*Attorney, Agent, or Firm*—Worrel & Worrel

[57] ABSTRACT

A new and distinct variety of plum tree which produces fruit which is mature for harvesting and shipment approximately September 20 to September 25 in the central San Joaquin Valley of Calif. which is very large for plum fruit, which is freestone by nature and which further exhibits a distinctive red and yellow coloration is very firm having very good storage and handling attributes.

1 Drawing Sheet

BACKGROUND OF THE NEW VARIETY

The present invention relates to a new and distinct variety of plum tree which will hereinafter be denominated varietally as 'October Sun' and more particularly to a plum tree which produces fruit of large size and very mild low acid taste having a distinctive red-yellow coloration which is mature for commercial harvesting and shipment approximately September 20 to September 25 is the San Joaquin Valley of central Calif. and which possesses superior storage and handling attributes.

ORIGIN AND ASEXUAL REPRODUCTION OF THE NEW VARIETY

The present variety of plum tree is a chance seedling of a mixed lot of seed from a ranch located in Del Rey, Calif. The seed was collected in late summer 1979 and planted in a nursery in Del Rey, Calif. in 1980. The plum tree hereof was discovered by the inventor in this nursery in 1983 when the first fruit was observed as being very late in ripening and having a very good flavor.

Buds of the new variety were collected in the winter of 1983 and 1984 and seedlings were budded to the new variety by the inventor in early spring 1984. The first fruit produced by the asexually reproduced trees of the new variety was observed in 1985 and was confirmed to have all of the distinctive characteristics of the parent plum tree of the new variety. Since the fruit ripened so late in the season, the trees were observed for several more seasons in an effort to determine if early rains would harm the fruit. It was determined that no such harm took place, that the fruit had an unusual firmness which contributed to the longevity of the fruit in storage and to its resistance to damage and that it was very easy to set a crop on the new variety of plum tree.

SUMMARY OF THE NEW VARIETY

The 'October Sun' plum tree is characterized as to novelty by producing a freestone fruit which is large with a very mild low acid taste. The fruit is very firm making it easy to handle at harvest time and still has a very good flavor. The fruit ripens for harvest and shipment approximately September 20 to September 25 in the central San Joaquin Valley of Calif. and has a very distinctive red and yellow coloration. The fruit has been discovered to have a very good shelf life without any breakdown retaining its flavor during such storage making it a good fruit to market during the month of October when there is very little fresh stone fruit on the market. As noted, the plum tree of the present variety is a chance seedling of a mixed lot of seed taken from an orchard of 'Lroda', 'Friar' and 'Highland Sun' plum trees. However, the present variety is substantially different from these varieties in both color and ripening date. The applicant is not aware of a known commercial variety with which the present variety is comparable in any meaningful respect.

BRIEF DESCRIPTION OF THE DRAWING

The accompanying drawing is a photograph showing fruit of the new variety including a first in side elevation and retaining its natural waxy coating, a second sectioned and laid open to show the stone cavity in one-half and the stone in place on the other half, a third in top plan view showing the stem cavity, a fourth in bottom plan view showing the apex end thereof, a fifth in side elevation with its waxy coating removed and a sixth in bottom plan view showing the apex end thereof; and representative foliage.

DETAILED DESCRIPTION

Referring more specifically to the pomological details of this new and distinct variety of plum tree, the following has been observed under the ecological conditions prevailing at the nursery which is located in Del Rey, Calif. All major color code designations are by reference to the Inter-Society Color Council-National Bureau of Standards color name charts.

TREE

Generally:

*Size.*—Not as upright as some, seem to spread more.

*Vigor.*—Very vigorous.

*Figure.*—Vigorous and spreads easily.

*Productivity.*—Annually produces very well. Will need thinning every year.

Trunk:

*Size.*—Normal.

*Surface texture.*—Normal rough.

*Bark color.*—(62 d gy br).

*Lenticels.*—Numbers — 10 to 12 large lenticels per square inch. Size — About 0.635 cm (¼ inch) in length. Color — (57 1 br).

Branches:

*Size.*—Normal.

*Surface texture.*—Normal.

*Color.*—Brown (62 d gy br).

*Lenticels.*—Numbers — 10 to 12 per square inch. Size — 0.635 cm (¼ inch) in length. Color — (57 1 br).

LEAVES

Size:

*Generally.*—Medium.

*Average length.*—8.255 cm (3¼ inches) to 10.16 cm (4 inches).

*Average width.*—3.81 cm (1½ inches) to 4.7625 cm (1⅞ inches).

Form: Lanceolate.

Color:

*Upwardly disposed surface.*—Medium green (127 gy 01 g).

*Downwardly disposed surface.*—Light green (122 qy yg).

Marginal form:

*Generally.*—Very finely doubly serrate.

Glandular characteristics: Not always found. If found, very small globose.

Petiole:

*Length.*—1.588 cm (⅝ inch).

*Width.*—0.159 cm (1/16 inch).

Stem glands:

*Form.*—If found, globose; very small.

*Position.*—Opposite to each other.

Stipules: None.

FLOWERS

Flower buds:

*Size.*—With white starting to show at apex, length 0.476 cm (3/16 inch) and diameter 0.476 cm (3/16 inch).

*Shape.*—Almost round in appearance.

*Petiole.*—About 0.635 cm (¼ inch) with white starting to show at apex.

*Other characteristics.*—Buds seem to develop in pairs, few will come out singly.

*Color.*—Light green (119 1 yg).

Flowers:

*Generally.*—Look elongated but are round.

*Date of bloom.*—February 20 to February 25 or about 6 to 8 days after Santa Rosa Plum Tree at Del Rey, Calif.

*Size.*—Generally — Each petal is 0.476 cm (3/16 inch) in length; 0.476 cm (3/16 inch) in width.

*Petiole.*—At full blossom, 0.9525 cm (⅜ inch) in length.

*Petals.*—Color — White (263 white).

FRUIT

Maturity when described: Ripe for commercial harvesting and shipment approximately September 20 to September 25 at Del Rey, Calif.

Size:

*Generally.*—Uniformity — Good.

*Average diameter.*—5.874 cm (2-5/16 inches) to 6.35 cm (2½ inches).

*Average transverse diameter in the suture plane.*—6.191 cm (2-7/16 inches) to 6.985 cm (2¾ inches).

*Average diameter transverse and at right angles to the suture plane.*—6.191 cm (2-7/16 inches) to 6.985 cm (2¾ inches).

Form:

*Uniformity.*—Good.

*Symmetry.*—Very large for plum; not full round, slightly elongated.

Suture:

*Generally.*—Very smooth, slightly recessed.

*Length.*—8.89 cm (3½ inches) to 10.16 cm (4 inches).

Ventral surface:

*Generally.*—Very rounded with no apex point.

Stem cavity:

*Generally.*—Elongated, not round.

Base: Rounded.

Stem:

*Length.*—1.588 cm (⅝ inch).

*Width.*—0.238 cm (3/32 inch).

Pistil point: Very smooth. No apex point.

Skin:

*Thickness.*—Normal; less than 0.039 cm (1/64 inch).

*Texture.*—Very smooth.

*Tendency to crack.*—None.

*Color.*—Skin is red (15m red) and yellow (101 1 yg.). Variability from yellow to red in skin coloration depending upon the extent of exposure to sun light during maturation.

*Flesh color.*—Light yellow (87 m.y.).

*Surface of pit cavity.*—Quite smooth.

*Color of pit cavity.*—(84 s.y.).

Juice production: Very juicy, mild in flavor and no acid.

Flavor: Mild to sweet, not tart or acid flavor.

Aroma: Slight.

Texture: Smooth.

Ripening: Even.

Eating quality: Very good.

Stone:

*Attachment.*—Almost full freestone.

*Fibers.*—Numbers — None.

*Size.*—Length — About 2.381 cm (15/16 inch). Width — 1.588 cm (⅝ inch). Thickness — 1.588 cm (⅝ inch).

*Form.*—Generally — Elongated and flat.

*Color.*—(88 d y) yellow.

*Base.*—Shape — Small, flat and narrow.

*Sides.*—Very slightly rough.

*Ridges.*—None.

Use: Fresh market.

Keeping quality: Has been kept in cold storage for over 30 days and on counter for 10 to 14 days and has held up very well and not lost flavor.

Harvesting: This fruit is very firm, making it easy to handle at harvest time and still have very good flavor. Rain has no effect on the quality of the fruit.

Shipping and handling qualities: This plum is quite firm, does not easily bruise. Should ship well.

Although the new variety of plum tree possesses the described characteristics noted above as a result of the growing conditions prevailing near Del Rey in the Central part of the San Jaoquin Valley of Central Calif., it is to be understood that variations of the usual magnitude and characteristics incident to changes in growing conditions, fertilization, pruning and pest control are to be expected.

Having thus described and illustrated my new variety of plum tree, what I claim as new and desire to be secured by Plant Letters Patent is:

1. A new and distinct variety of plum tree substantially as illustrated and described which produces fruit which is mature for commercial harvesting and shipment approximately September 20 to September 25 in the San Joaquin Valley of central Calif. is of large size and very firm flesh with skin of a distinctive red-yellow coloration and which further has noteworthy shipping and handling characteristics.

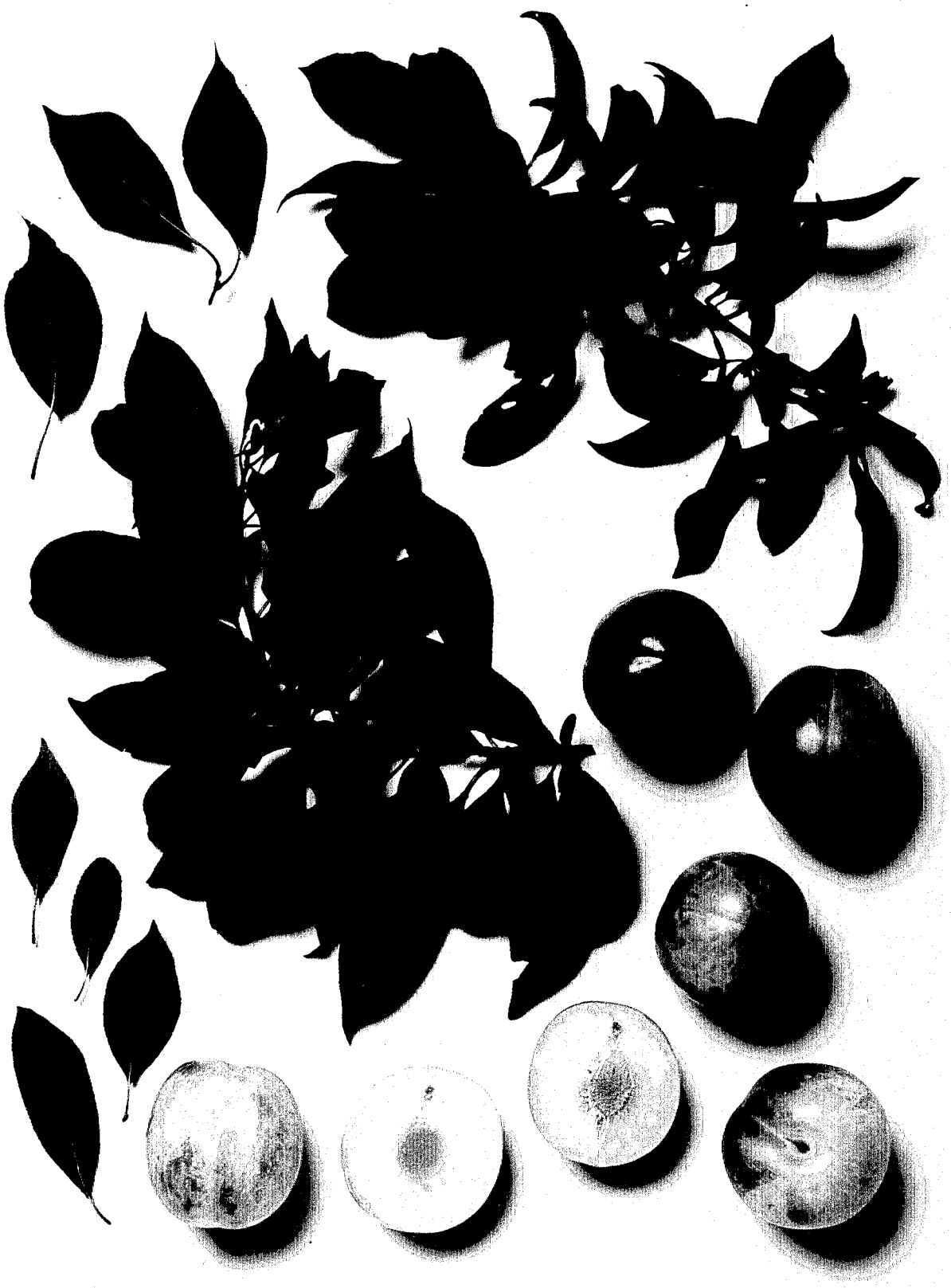

* * * * *